United States Patent [19]

Wu

[11] Patent Number: 4,570,618

[45] Date of Patent: Feb. 18, 1986

[54] INTERVERTEBRAL BODY WIRE STABILIZATION

[75] Inventor: Kent K. Wu, Royal Oak, Mich.

[73] Assignee: Henry Ford Hospital, Detroit, Mich.

[21] Appl. No.: 555,361

[22] Filed: Nov. 23, 1983

[51] Int. Cl.⁴ .......................... A61F 5/00; A61F 5/04
[52] U.S. Cl. .................... 128/69; 128/92 B; 128/92 E
[58] Field of Search ............ 128/69, 92 R, 92 A, 128/92 G, 92 E, 92 B

[56] References Cited

U.S. PATENT DOCUMENTS

| | | | |
|---|---|---|---|
| 3,255,747 | 6/1966 | Cochran et al. | 128/92 R |
| 3,693,616 | 9/1972 | Roof et al. | 128/69 |
| 3,877,424 | 4/1975 | Murray | 128/92 A |
| 3,915,160 | 10/1975 | Lode et al. | 128/69 |
| 4,003,376 | 1/1977 | McKay et al. | 128/69 |
| 4,078,559 | 3/1978 | Nissinen | 128/69 |
| 4,112,935 | 9/1978 | Latypov et al. | 128/69 |

FOREIGN PATENT DOCUMENTS

| | | | |
|---|---|---|---|
| 2295725 | 7/1976 | France | 128/92 A |
| 2086231 | 5/1982 | United Kingdom | 128/92 A |
| 733668 | 5/1980 | U.S.S.R. | 128/92 A |

Primary Examiner—Robert Peshock
Assistant Examiner—C. W. Shedd
Attorney, Agent, or Firm—Barnes, Kisselle, Raisch, Choate, Whittemore & Hulbert

[57] ABSTRACT

The method and apparatus of stabilizing the spine wherein a bone graft has been provided between spaced vertebral bodies which comprises engaging preformed wire members having loops connected by wire with each loop engaging the transverse process of a vertebra, forming the wire connecting loops in an arch extending posteriorly of the lamina, and packing bone cement about the wire members and longitudinally between the lamina.

9 Claims, 7 Drawing Figures

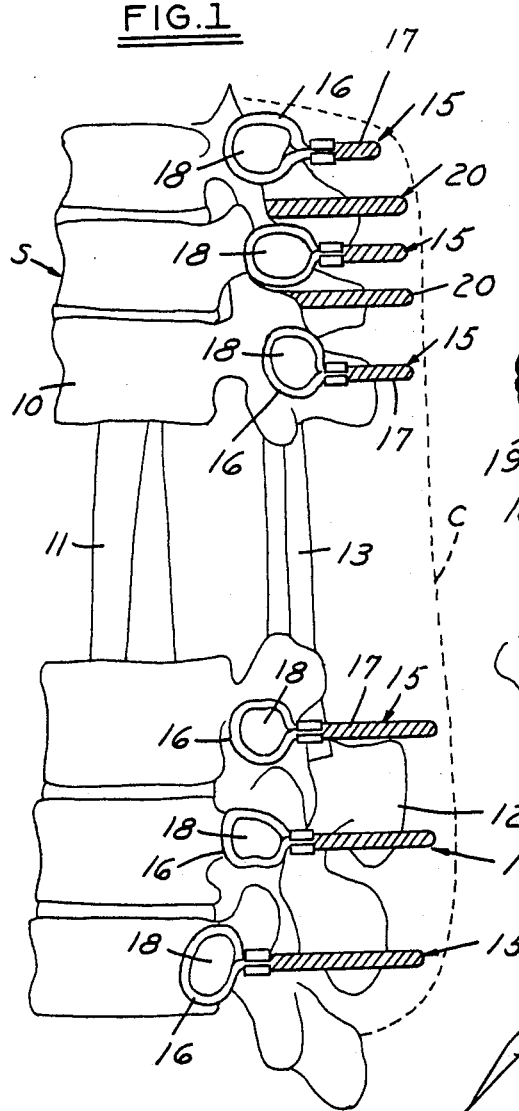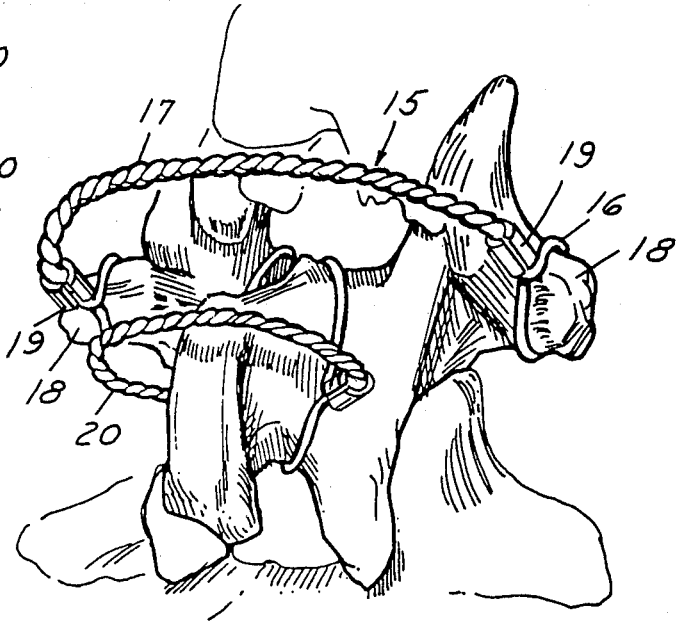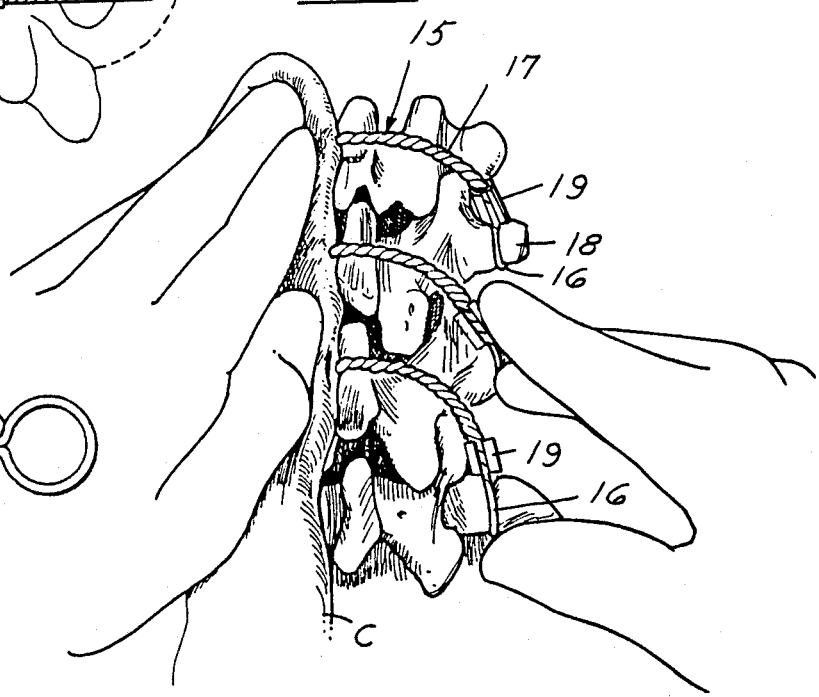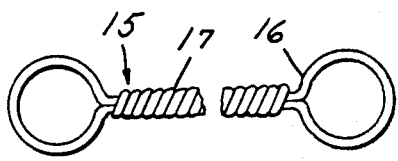

INTERVERTEBRAL BODY WIRE STABILIZATION

This invention relates to stabilization of the spine where portions of the spine have been removed and replaced by a bone graft.

BACKGROUND AND SUMMARY OF THE INVENTION

In the treatment of disease or injury to the spine, it is often necessary to remove portions of the spine and replace the removed portions by bone grafts in a process known as bone fusion.

Inasmuch as the healing of the bone fusion takes time, it is desirable to provide stabilization to the spine that will remain in position not only during the healing but also after the healing.

Among the objectives of the present invention are to provide a method and apparatus for stabilizing the spine which will effectively provide substantially immediate stabilization not only where vertebral bodies are removed but also where vertebrae are removed.

In accordance with the invention, the method of stabilizing the spine wherein a bone graft has been provided between spaced vertebral bodies which comprises engaging preformed wire members having loops connected by wire with each loop engaging the transverse process of a vertebra, forming the wire connecting loops in an arch extending posteriorly of the lamina, and packing bone cement about the wire members and longitudinally between the lamina.

DESCRIPTION OF THE DRAWINGS

FIG. 1 is a side elevational view of a portion of a spine that has been stabilized in accordance with the invention.

FIGS. 2 and 3 are fragmentary perspective views showing stpes in the practice of the method.

FIG. 4 is a plan view of a wire member utilized in the invention.

DESCRIPTION

Figure 5:
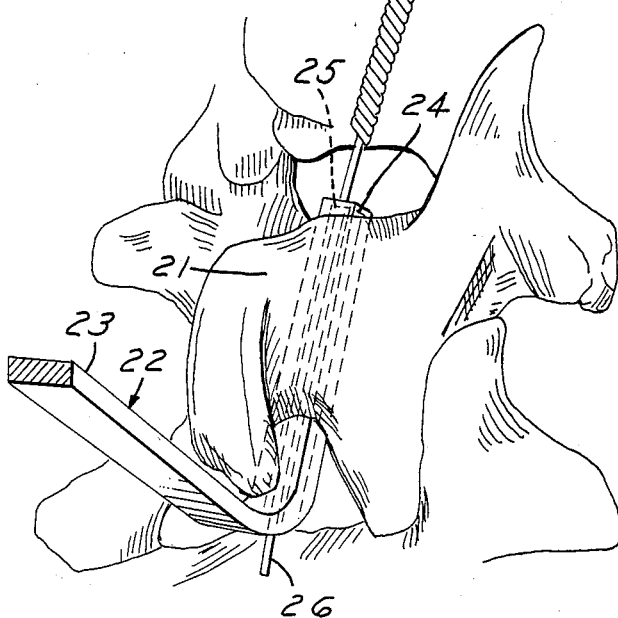
FIGS. 5 and 6 are fragmentary perspective views showing further steps in the practice of the method.

Referring to FIGS. 1–3, there is shown a spine S wherein vertebral bodies 10 have been removed and replaced by a bone graft 11 and vertebra 12 have been removed and replaced by a bone graft 13.

In accordance with the invention, wire arches 15 are provided and extend rearwardly from the vertebra that remain and bone cement is applied over the wire arches 15 and in the space between the wire arches 15 so that when it sets it will strengthen the bone grafts.

As shown in FIG. 4, each arch 15 is formed of a wire member that comprises spaced loops 16 interconnected by a wire portion 17 that can be readily bent to from the arch. The loops 16 are placed over the transverse processes 18 and C clips 19 are utilized to tightly clamp the loops 16 on the vertical processes 18. The wire members are preferably made from a single length of wire which is bent intermediate its ends to form the loops and then the remaining ends of the wires are twisted together to form the interconnecting wire portion 17.

After all of the wire members 15 are placed in position, bone cement C such as methyl methacrylate is applied over the arches 15 and between the arches 15.

If desired additional support may be provided by wire devices 20 for each lamina. These are formed in place by threading a wire about the lamina 21 and thereafter twisting the ends together to form the interconnecting portion as shown in FIG. 2.

A preferred method of passing the wire about the lamina is by utilization of a sublaminar tool such as disclosed in U.S. patent application Ser. No. 521,681 filed Aug. 10, 1983 which is incorporated herein by reference.

Figure 6:
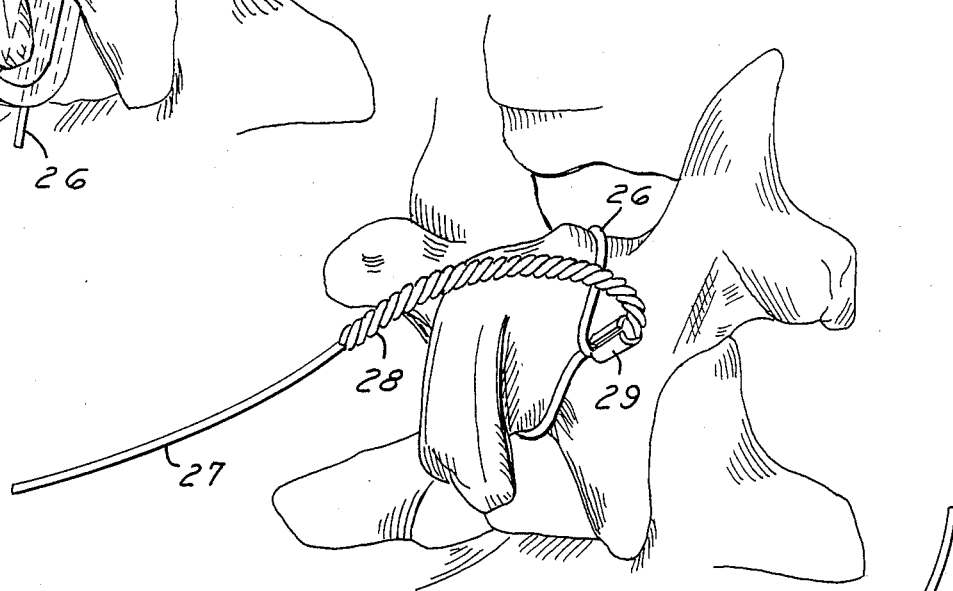
Figure 7:
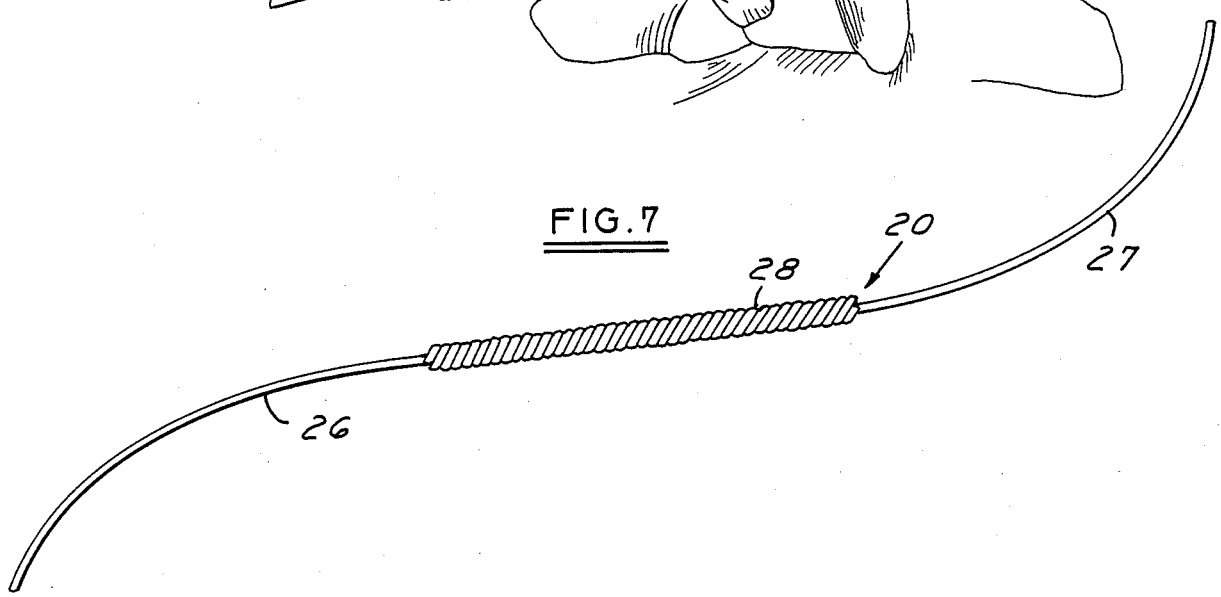
FIG. 7 is a plan view of an additional wire member utilized in the invention.

As shown in FIG. 5, a tool 22 having a handle 23 and a projection 24 with an opening 25 therein is utilized and the tool 22 is inserted between the ligaments and the posterior of the lamina. While the tool 22 is in position, one end 26 of the wire 20 is passed through the opening 25 from the top to the bottom and twisted about the lamina 21 as shown in FIG. 6. The other end 27 of the wire device is then similarly passed about the other lamina 21 and twisted about the wire. The intermediate portion of the wire device has an additional wire 28 twisted about its central portion to provide rigidity. A small metal clamp 29 can be utilized to fix each end as in the other form of wire device.

I claim:

1. The method of stabilizing the spine wherein a bone graft has been provided between spaced vertebral bodies which comprises
    engaging preformed wire members having loops connected by wire with each loop engaging the transverse process of a vertebra,
    forming the wire connecting loops in an arch extending posteriorly of the lamina, and
    packing bone cement about the wire members and longitudinally between the lamina.

2. The method set forth in claim 1 including the step of clamping each loop tightly about the transverse process.

3. The method set forth in claim 1 wherein the portion of the wire between the loops is twisted.

4. The method set forth in claim 1 wherein said wire member comprises a single length of wire.

5. The method set forth in claim 1 including the step of forming additional arches by looping a wire member through the laminae prior to applying the bone cement.

6. The method set forth in claim 5 wherein said additional arch is formed by passing one end of a length of wire under a lamina from the top to the base of the posterior of a lamina, twisting said one end about the lamina to define a loop, passing the other end of the wire under the opposite lamina from the top to the base and twisting the free end of the other end to form a loop about the other lamina.

7. The method set forth in claim 6 including the step of clamping each loop tightly about the respective lamina.

8. A wire stabilizing device for use in stabilizing the vertebra of a spine which comprises spaced loops and an interconnecting wire member which can be bent into the form of an arch, said interconnecting wire member being made of twisted wires.

9. A wire stabilizing device for use in stabilizing the vertebra of a spine which comprises spaced loops and an interconnecting wire member which can be bent into the form of an arch, said stabilizing device being made of a single length of wire bent intermediate its ends to form loops with the ends twisted about other portions of the wire to form an interconnecting twisted portion.

* * * * *